US00PP20947P2

(12) United States Plant Patent
Johnson

(10) Patent No.: US PP20,947 P2
(45) Date of Patent: Apr. 27, 2010

(54) ***LIGULARIA* PLANT NAMED 'LAST DANCE'**
(50) Latin Name: *Ligularia hybrid*
Varietal Denomination: Last Dance

(75) Inventor: Ozzie Johnson, Marietta, GA (US)

(73) Assignee: Itsaul Plants, LLC, Alpharetta, GA (US)

( * ) Notice: Subject to any disclaimer, the term of this patent is extended or adjusted under 35 U.S.C. 154(b) by 0 days.

(21) Appl. No.: 12/315,447

(22) Filed: Dec. 3, 2008

(51) Int. Cl.
*A01H 5/00* (2006.01)

(52) U.S. Cl. ..... Plt./448

(58) Field of Classification Search ..... Plt./263, Plt./448
See application file for complete search history.

*Primary Examiner*—Susan B McCormick Ewoldt
(74) *Attorney, Agent, or Firm*—Penny J. Aguirre

(57) ABSTRACT

A new cultivar of *Ligularia*, 'Last Dance', an interspecific hybrid of *Ligularia hiberniflora* and *Farfugium japonicum*, characterized by its medium sized leaves with dentate margins, its compact plant habit, and its abundant bright yellow inflorescences that are densely arranged on well-branched scapes.

2 Drawing Sheets

Botanical classification: *Ligularia* hybrid.
Cultivar designation: 'Last Dance'.

BACKGROUND OF THE INVENTION

The present invention relates to a new and distinct cultivar of *Ligularia*, botanically an interspecific hybrid, and hereinafter referred to by the cultivar name 'Last Dance'.

The new cultivar resulted from a cross made in the Inventor's garden in Marietta, Ga. in 1998 between an unnamed plant of *Ligularia hiberniflora* as the female parent and an unnamed plant of *Farfugium japonicum* (syn. *Ligularia tussilaginea*) as the male parent (both unpatented). The new cultivar was selected as a single unique plant from the resulting seedlings by the Inventor in 1998.

Asexual reproduction of the new cultivar was first accomplished by division by the Inventor in Marietta, Ga. in 2000. Asexual reproduction of the new culthar by division and tissue culture has shown that the unique features of 'Last Dance' are stable and reproduced true to type in successive generations.

SUMMARY OF THE INVENTION

The following traits have been repeatedly observed and represent the characteristics of the new cultivar. These attributes in combination distinguish 'Last Dance' as a new and unique cultivar of *Ligularia*.

1. 'Last Dance' has leaves that intermediate in size in comparison to its parents.
2. 'Last Dance' has leaves with a dentate margin.
3. 'Last Dance' has a compact habit.
4. 'Last Dance' has yellow composite inflorescences that are densely clustered on well-branched scapes.

'Last Dance' differs from its female parent, *Ligularia hiberniflora*, in having larger leaves, larger and more abundant inflorescences, and a taller plant height. 'Last Dance' differs from its male parent, *Farfugium japonica*, in having leaves with a dentate margin rather than an entire margin, in having a more compact plant habit, in being shorter in plant height and in having inflorescences that are more abundant and compact and have a greater number of ray florets that are borne on more well-branched scapes. 'Last Dance' can also be compared to cultivars of *Farfugium japonica*, 'Aureomaculata' and 'Jitsuko's Star'. 'Aureomaculata' differs from 'Last Dance' in being shorter in height, having spotted foliage, a lower bloom count, leaf edges that are undulated rather than dentate, and an earlier bloom season. 'Jitsuko's Star' differs from 'Last Dance' in having more heart-shaped and cupped foliage, in being taller in height in bloom, and in having double flowers with star-like ray floret petals.

BRIEF DESCRIPTION OF THE DRAWING

The accompanying colored photographs illustrate the overall appearance and distinct characteristics of the new *Ligularia*. The photographs in the figures were taken of four-year-old plants of 'Last Dance' as grown in Marietta, Ga.

Figure 1:
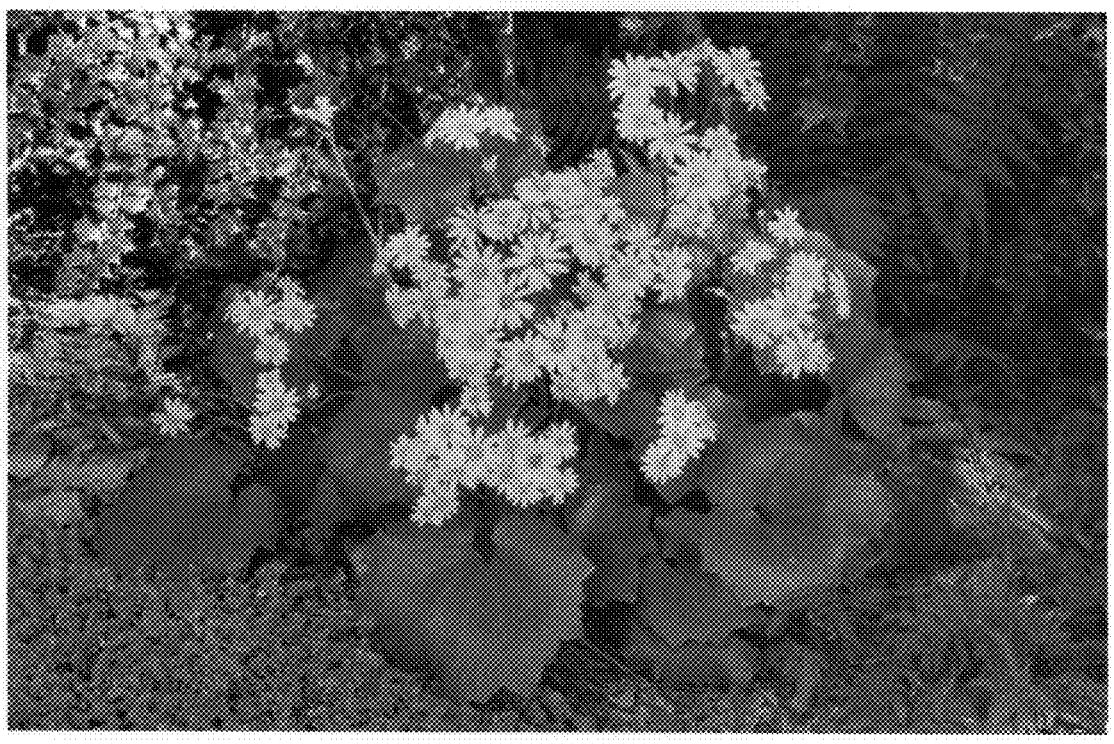
FIG. 1 provides a view of the habit and foliage characteristics of the new cultivar in bloom.
Figure 2:
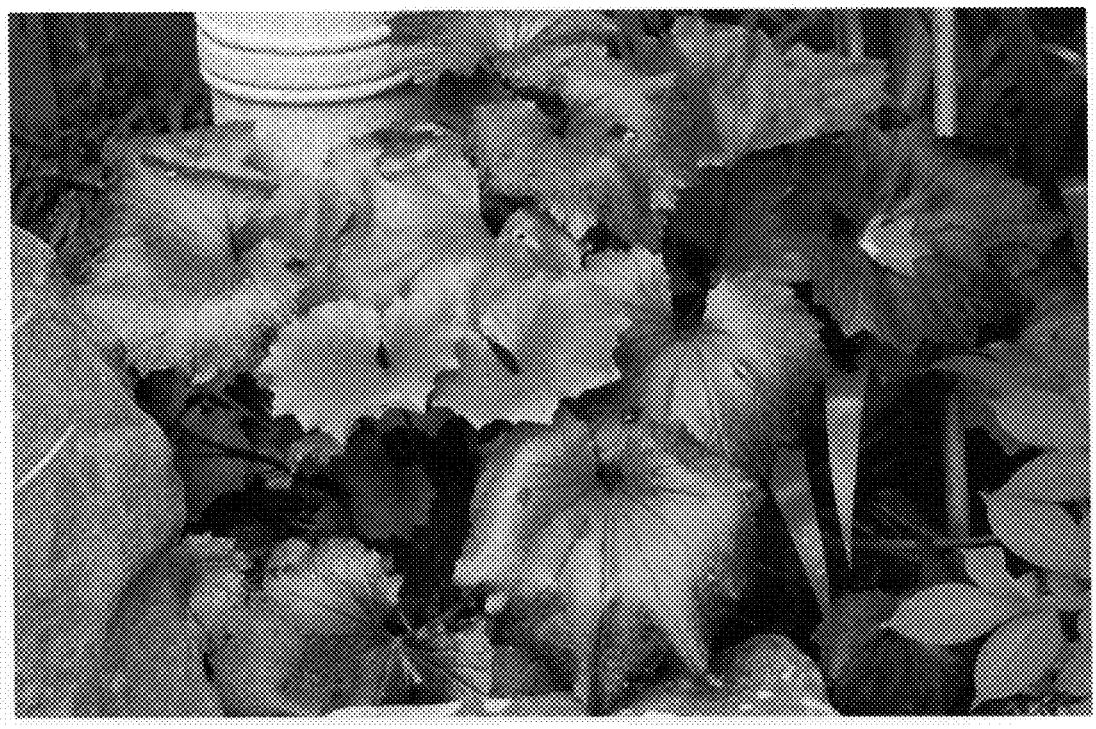
FIG. 2 shows a close-up view of the foliage in mid summer and FIG. 3 provides a close-up view of the flowers.
Figure 3:
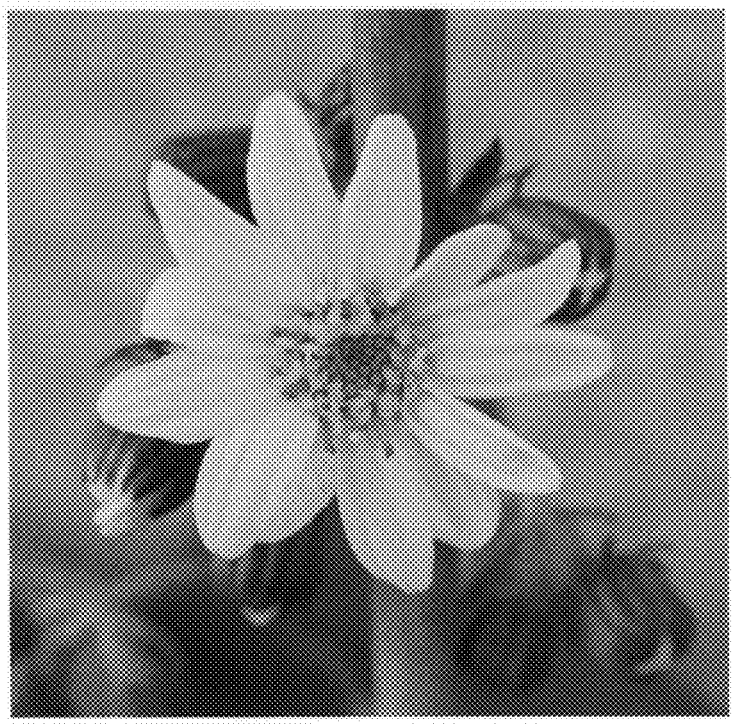

The colors in the photograph may differ slightly from the color values cited in the detailed botanical description, which accurately describe the colors of the new *Ligularia*.

DETAILED BOTANICAL DESCRIPTION OF THE PLANT

The following is a detailed description of the new cultivar as observed for eight years in Marietta, Ga. with the detailed botanical data collected on two year-old plants of the new cultivar as grown outdoors in a 2-quart container in Alpharetta, Ga. The phenotype of the new cultivar may vary with variations in environmental, climatic, and cultural conditions, as it has not been tested under all possible environmental conditions. The color determination is in accordance with the 2007 R.H.S. Colour Chart of the Royal Horticultural Society, London, England, except where general color terms of ordinary dictionary significance are used.

General description:

*Blooming habit.*—Blooms for about one month in mid fall in Georgia.

*Plant habit.*—Clump forming, robust, herbaceous perennial, compact, with blooms held above the foliage.

*Height and spread.*—Reaches about a height of 30 to 40 cm in bloom (12 to 18 inches) and 45 to 61 cm (18 to 24 inches) in width.

*Hardiness.*—U.S.D.A. Zones 5 to 10.

*Diseases and pests.*—Disease and pest free under the conditions tested.

*Root description.*—Fibrous.

*Branching habit.*—Basal foliage on long petioles.

*Propagation.*—In vitro propagation is the preferred method, division is also possible.

*Growth rate.*—Moderate.

Foliage description:

*Leaf shape.*—Broadly ovate to orbicular.

*Leaf division.*—Simple.

*Leaf base.*—Cordate.

*Leaf apex.*—Broadly acute.

*Leaf venation.*—Palmate, uniquely conspicuous, color on upper surface 144B near base with other regions matching leaf color, color on lower surface N77C, surface of veins are glabrous on upper surface and pubescent on lower surface.

*Leaf margins.*—Dentate with about 7 dentations per side on leaf 10 cm in length, dentations have small mucronate tip, slightly undulating.

*Leaf attachment.*—Petiolate.

*Leaf arrangement.*—Basal rosette.

*Leaf orientation.*—Held nearly horizontal to petiole,

*Leaf surface.*—Glabrous on upper surface and puberulent on lower surface.

*Leaf color.*—Emerging leaves upper surface; 146A, emerging leaves lower surface; 148B, mature leaves upper surface; 137B and becoming flushed and with spots of N92A, maturing leaves lower surface; 138C and becoming flushed with N92A, fall leaves upper surface; blend of N137B, 137A and 137B with a very narrow margin of N92A, fall leaves lower surface; 148B and lightly suffused with N92A and a very narrow margin of N92A.

*Leaf size.*—Matures to an average of 20 to 23 cm in length and width.

*Leaf quantity.*—New leaves continuously produced, average of 15 on a single division in a 2-quart container in late summer.

*Petioles.*—Oval in shape, orientation ranges from vertical to horizontal, average of 9 cm in length and 4 mm in width on mature leaves, matures to 187A in color, surface is tomentose with hairs 199C in color.

Inflorescence description:

*Type.*—Capitulum, heterogamous with ray florets around the head margin and disk florets in the center, forming a radiant head, arranged in corymbs on branched scapes.

*Capitulum number.*—Average of 13 per branched scape (peduncle).

*Lastingness of inflorescence.*—About 3 weeks until senescence of ray florets, disk flowers are persistent, a cut flower will last about 7 days.

*Capitulum size.*—Matures to about 2.5 cm in depth and 5 cm in diameter, disk size is about 1.8 cm in diameter.

*Fragrance.*—Slight rose scent.

*Phyllary.*—Arranged in 2 rows, outer row; average of 6, 187A in color, linear in shape, about 7 mm in length and 1.5 mm in width, glossy surface, inner row; about 12, fused into a campanulate involucre about 1.5 cm in length and 1.3 cm in width, un-fused acute apex is about 3 mm in length and 2 mm in width, color is 144A with apex 187A, surface is sparsely covered with hairs and semi-glossy.

*Buds.*—Broadly oblong in shape, average of 1.1 cm in diameter and 1.3 cm in depth, 137C in color and suffused with 187A with outer phyllary 187A in color and apex of 13B in color.

*Peduncle.*—Branched, main peduncle about 22 cm in length and an average of 5.5 mm in width with an average of 5 branches ranging from 1.5 to 11 cm in length and an average of 3 mm in width, 178A in color, surface is tomentose with hairs 199C in color, average of 3 leaves, same coloration and surface as basal leaves, sessile, primarily lanceolate in shape with elongated and truncate base and acute apex, an average of 3 cm in length in length and 7 mm in width.

*Pedicels.*—187A in color, 5 mm to 1.2 cm in length and an average of 2.5 mm in width, color is 199A in color due to surface that is heavily tomentose.

*Ray florets* (*female*).—Average of 13, narrowly elliptic in shape, vertical ridges on both surfaces, about 2.4 cm in length with blade about 2 cm in length and 7 mm in width and narrow base about 7 mm in length and 1 mm in width, rounded apex and slightly emarginated, cuneate base, entire margin except apex, glabrous in texture, initially held upright about 70° from horizontal and become horizontal to slightly reflexed as they mature, color of upper and lower surface; 12A with narrow base enclosing the pistil 145D in color.

*Disk flowers* (*bisexual*).—About 40, tubular in shape, arranged spirally on a conical receptacle, about 1.7 cm in length and 4 mm in width, pappus comprised of about 30 bristles about 7 mm in length and 199C in color; 153B in mass prior to opening, 12A in color when open, comprised of fused petals that are 12A at apex and becoming 155A at base.

Reproductive organs:

*Gynoecium.*—Pistil; 1, about 1.1 cm in length and 1.5 mm in width, style; 0.3 mm in width and 9 mm in length, 145D in color and translucent, surrounded by stamens, stigma; bifid, each arm is reflexed and about 1 mm in length and 12A in color, ovary; inferior, about 3 mm in length, 1 mm in width, and 155A in color.

*Androcoecium.*—Stamens; 4, un-fused, coherent in cylinder around style, anthers; 4 mm in length and 0.3 mm in width, basifixed, dehisced longitudinally, 163A in color with apex 165A, filaments; 5 mm in length, 0.3 mm in width, 145C in color, pollen; not readily distinguishable.

*Fruit.*—Development not observed.

It is claimed:

1. A new and distinct cultivar of *Ligularia* plant named 'Last Dance' as herein illustrated and described.

* * * * *